(12) United States Patent
Mottram et al.

(10) Patent No.: US 8,979,757 B2
(45) Date of Patent: Mar. 17, 2015

(54) METHOD AND SYSTEM FOR MONITORING THE CONDITION OF LIVESTOCK

(75) Inventors: Toby Mottram, Devon (GB); Paul Edward George Devlin, Larbert (GB)

(73) Assignee: ITI Scotland Ltd., Glasgow (GB)

( * ) Notice: Subject to any disclaimer, the term of this patent is extended or adjusted under 35 U.S.C. 154(b) by 1142 days.

(21) Appl. No.: 12/226,464

(22) PCT Filed: Apr. 18, 2007

(86) PCT No.: PCT/GB2007/001423
§ 371 (c)(1),
(2), (4) Date: Feb. 12, 2009

(87) PCT Pub. No.: WO2007/119070
PCT Pub. Date: Oct. 25, 2007

(65) Prior Publication Data
US 2010/0030036 A1    Feb. 4, 2010

(30) Foreign Application Priority Data
Apr. 18, 2006 (GB) .................................. 0607657.4

(51) Int. Cl.
*A61B 5/00* (2006.01)
*A01K 11/00* (2006.01)
(Continued)

(52) U.S. Cl.
CPC ............... *A61B 5/0011* (2013.01); *A01K 11/00* (2013.01); *A01K 11/001* (2013.01); *A01K 11/007* (2013.01); *A01K 11/008* (2013.01); *A01K 29/005* (2013.01); *A61B 5/0002* (2013.01); *A61B 5/02055* (2013.01); *A61B 5/02438* (2013.01); *A61B 5/1112* (2013.01);
(Continued)

(58) Field of Classification Search
USPC .................................................. 600/300–301
See application file for complete search history.

(56) References Cited

U.S. PATENT DOCUMENTS 6,441,747 B1    8/2002    Khair et al.
6,868,804 B1    3/2005    Huisma et al.
(Continued)

FOREIGN PATENT DOCUMENTS

CA    1296068    2/1992
EP    0808567    11/1997
(Continued)

OTHER PUBLICATIONS

Blanc and Berger, "Comparison of Two Automatic Methods for Measuring Grazing Behaviour," Ann. Zootech. 44, Suppl. 235, 1995.
(Continued)

*Primary Examiner* — William Thomson
*Assistant Examiner* — Bobby Soriano
(74) *Attorney, Agent, or Firm* — Vinson & Elkins

(57) ABSTRACT

A method and system for monitoring the condition of livestock comprises a plurality of sensors (115, 103, 113, 111, 107, 105) for sensing a plurality of different behavioral parameters of an animal. The sensed data is transmitted by a unit (115), wirelessly, t a central processor (119) and a plurality of status conditions of the animal is determined on the basis of the transmitted, sensed data such as the onset of parturition, fertility status and other health status conditions. The unit (115) may be permanently worn by the animal and may keep an electronic record of the status conditions of the animal.

22 Claims, 4 Drawing Sheets

(51) Int. Cl.

| | | |
|---|---|---|
| A01K 29/00 | (2006.01) | |
| A61B 5/0205 | (2006.01) | |
| A61B 5/024 | (2006.01) | |
| A61B 5/11 | (2006.01) | |
| A61B 5/145 | (2006.01) | |
| A61D 17/00 | (2006.01) | |
| A61B 5/01 | (2006.01) | |
| A61B 5/0488 | (2006.01) | |
| A61B 5/08 | (2006.01) | |
| A61B 10/00 | (2006.01) | |
| A61B 19/00 | (2006.01) | |

(52) U.S. Cl.
CPC ........... *A61B5/14539* (2013.01); *A61B 5/6815* (2013.01); *A61B 5/6822* (2013.01); *A61B 5/6828* (2013.01); *A61B 5/6838* (2013.01); *A61D 17/002* (2013.01); *A61D 17/006* (2013.01); *A61D 17/008* (2013.01); *A61B 5/0024* (2013.01); *A61B 5/01* (2013.01); *A61B 5/0488* (2013.01); *A61B 5/1107* (2013.01); *A61B 5/1114* (2013.01); *A61B 5/1116* (2013.01); *A61B 5/1118* (2013.01); *A61B 5/14507* (2013.01); *A61B 5/4519* (2013.01); *A61B 5/4866* (2013.01); *A61B 5/6831* (2013.01); *A61B 5/6833* (2013.01); *A61B 5/7282* (2013.01); *A61B 5/0816* (2013.01); *A61B 10/0012* (2013.01); *A61B 2019/448* (2013.01); *A61B 2503/40* (2013.01)
USPC .......................................... 600/301; 119/421

(56) References Cited

U.S. PATENT DOCUMENTS

| | | | |
|---|---|---|---|
| 7,335,168 B2* | 2/2008 | Rugg | 600/595 |
| 7,878,149 B2 | 2/2011 | Voronin et al. | |
| 7,992,521 B2* | 8/2011 | Bocquier | 119/174 |
| 2002/0010390 A1* | 1/2002 | Guice et al. | 600/300 |
| 2004/0059195 A1* | 3/2004 | Ridenour | 600/300 |
| 2004/0078219 A1* | 4/2004 | Kaylor et al. | 705/2 |
| 2004/0100376 A1* | 5/2004 | Lye et al. | 340/539.12 |
| 2004/0133081 A1 | 7/2004 | Teller et al. | |
| 2005/0059870 A1* | 3/2005 | Aceti | 600/340 |
| 2005/0101841 A9* | 5/2005 | Kaylor et al. | 600/300 |
| 2006/0155172 A1* | 7/2006 | Rugg | 600/300 |
| 2007/0021945 A1 | 1/2007 | Riskey et al. | |

FOREIGN PATENT DOCUMENTS

| | | |
|---|---|---|
| GB | 2347503 | 9/2000 |
| WO | WO 95/32616 | 12/1995 |
| WO | WO 99/07216 | 2/1999 |
| WO | WO 00/64245 | 11/2000 |

OTHER PUBLICATIONS

Berger, et al., Proceedings of the 1st International Symposium on Physiology and Ethology of Wild and Zoo Animals. Suppl. II, p. 14-17, 1997.

Scheibe, et al., Applied Animal Behaviour Science 55:195-211, 1998.

Brehme, et al., "Oestrus Detection in Cattle," Landtechnik 58:106-107, 2003.

Nagl, et al., "Wearable Sensor System for Wireless State-of-Health Determinatio in Cattle," 3rd Joint EMBS-BMES Conference, Cancun, Mexico, Sep. 2003.

Warren, et al., "A Distributed Infrastructure for Veterinary Telemedicine," 3rd Joint EMBS-BMES Conference, Cancun, Mexico, Sep. 2003.

Brehme, et al., "Safer Oestrus Detection with Sensor-Aided ALT-Pedometer," Landtechnik 59:230-231, 2004.

Hildreth, "Biomedical Sensor System for Continuous Wireless State-of-Health Determination in Cattle," Southwest Texas Cattle Ranchers Association, South Padre Island, TX, 2004.

Warren, et al., AMVA Annual Convention, Pennsylvania Convention Center, Philadelphia, PA, Jul. 24-28, 2004.

Schoenig, et al., 26th Annual Conference of the IEEE EMBS, St. Francis Hotel on Union Square, San Francisco, CA, Sep. 1-5, 2004.

IceTagAnalyzer TM, User Manual, IceRobotics, Scottish Microelectronics Centre, The King's Buildings, West Mains Road, Edinburgh, EH9 3JF, Scotland, 2005.

Warren, et al., 10th Annual Meeting and Exposition of the American Telemedicine Association, Denver, CO, Apr. 17-20, 2005.

International Search Report, International Patent Application No. PCT/GB2007/001423, Jul. 30, 2007.

Examination Report, Canadian Patent Application No. 2,649,807, dated Jun. 5, 2013.

* cited by examiner

METHOD AND SYSTEM FOR MONITORING THE CONDITION OF LIVESTOCK

This application is a national stage application under 35 U.S.C. §371 of co-pending International Patent Application Number PCT/GB2007/001423, filed Apr. 18, 2007, which claims the benefit of Great Britain Patent Application Serial No. 0607657.4, filed Apr. 18, 2006, each of which is hereby incorporated by reference in their entireties, as if set forth below.

TECHNICAL FIELD

The present invention relates to a method and system for monitoring the condition of livestock. In particular, it relates to remotely monitoring the behavioural and physiological states of livestock to determine their welfare, health and fertility condition.

BACKGROUND OF THE INVENTION

With increasing awareness of health related issues concerning livestock and the significant losses that arise from poor fertility management, the farming industry has been forced to adapt in maintaining accurate records of livestock. As the size of farms increase, the ability of a stockman to keep records and track individual animals becomes increasingly difficult. There are many known systems for electronically tagging animals for identification purposes etc. Identification data is held in a unit worn by the animal in a neck collar, ear tag or injected transponder or the like. The data can be extracted as required at fixed or mobile locations.

It is also known to utilise such tags to collect data relating to activities of the animal, for example U.S. Pat. No. 5,857,434. U.S. Pat. No. 5,857,434 discloses detection of oestrus in dairy cattle. A transponder unit worn in a collar around the animal's neck detects the movement of the animal. During oestrus, the animal becomes agitated and moves around more frequently. This increased activity is detected and transmitted, along with identification data for the animal, to a central processor. The data is then processed and analysed to establish whether oestrus is detected and this is indicated to the stockman. The transponder merely collects the movement data of the animal. This data is then transmitted and centrally processed. The transponder does not detect oestrus. Further only a single condition, oestrus, is monitored and the system does not provide data concerning other health related matters.

Further some existing systems require sensors to be attached invasively which is distressing to the animal and requires the skill of a veterinary surgeon. Further such forms of attachment to the animal have limited ability to transmit information from the animal for use by the stockman.

Further existing systems, such as that disclosed by GB 2347503 and CA 1296068, comprise a range of sensors for monitoring the physiological parameters of an animal for determining the health of the animal. However, these require complex and, invariably, temperamental sensory instruments in order to monitor the physiological parameters making the system overall very expensive and hence impractical for monitoring all animals in a very large herd or group in a farming environment.

Furthermore due to the complexity of these systems, they require professional assistance, such as a veterinary surgeon, to set up, program and maintain the system which is impractical for an extremely large number of animals. Further, as such systems monitor physiological parameters, it is less intuitive to the stockman, who traditionally relies on observation to monitor health, to confirm the condition indicated by the system, thus making it more difficult for the stockman to verify the accuracy of the system.

Further, in monitoring the condition of livestock, a key period for health monitoring in cattle, sheep, horses and pigs is in the period immediately before and after parturition. None of the existing systems disclose specific monitoring during such periods.

At present there is no system that can do any of the condition based monitoring of cattle necessary to improve both the health and fertility monitoring of animals. Monitoring is still by human visual observation as it has been since the first domestication of animals. However, it has become increasingly desirable for better management of livestock, in particular health monitoring in livestock in the period immediately before and after parturition and to reduce losses from dystocia, hypocalcaemia and other diseases.

It has also become increasingly desirable to reduce time lost moving animals unnecessarily for veterinary examination. Further, it is desirable to provide earlier intervention in cases of metritis and lameness and thus improve welfare and possibly productivity of animals such as dairy cattle as well as provide improved oestrus detection.

With the increasing scale of farming, it has become increasingly difficult and impractical for stockmen to rely on traditional observation techniques to ensure health and welfare of their stock. There has therefore been an increasing need for additional monitoring systems to be utilised.

SUMMARY OF THE INVENTION

The invention seeks to provide remote, continuous monitoring of various parameters relating to the condition of livestock, such as cattle, sheep, pigs, horses and the like which mitigates the above mentioned disadvantages.

This is achieved according to an aspect of the present invention by a method for monitoring the condition of livestock, the method comprising the steps of: sensing a plurality of orientation and movement parameters of a subject; deriving a plurality of different behavioural parameters of the subject from the sensed plurality of orientation and movement parameters; determining a plurality of status conditions of the subject from the derived behavioural parameters; and transmitting the determined plurality of status conditions, wirelessly, to a central computer.

This is also achieved according to an aspect of the present invention by a system for monitoring the condition of livestock, the system comprising: a plurality of sensors for sensing a plurality of orientation and movement parameters of a subject; processing means for deriving a plurality of different behavioural parameters of the subject from the sensed plurality of orientation and movement parameters and determining a plurality of status conditions of the subject; at least one transmitter for transmitting the determined plurality of status conditions, wirelessly, to a central computer.

In this respect, behavioural parameters are those parameters relating to the behaviour of a subject. In particular it relates to parameters concerning the action and response of a subject to stimulation or its environment.

Further, this is achieved according to another aspect of the present invention by a device for monitoring the condition of livestock, the device comprising means for attaching the device to a subject; a plurality of sensors for sensing a plurality of orientation and movement parameters of the subject; processing means for deriving a plurality of different behavioural parameters of the subject from the sensed plurality of orientation and movement parameters and determining a plurality of status conditions of the subject; and a transceiver for transmitting the determined plurality of status conditions, wirelessly, to a central computer.

The monitor worn by the subject (animal) collates and processes the data in respect of the detected parameters of the livestock. The monitor transmits the data; say for example, via a local area network to a processor, which may in turn be linked via wireless communication to a central data processor and storage device. The data may be contained in a local database for use by the stockman and may also be contained in a national or veterinary health information database for wider reference and analysis. On the basis of the detected parameters, a plurality of status conditions, such as for example, oestrus, onset of parturition, lameness, disease, can be derived as an indication of the overall condition of the animal. Since behavioural parameters are monitored, the system is less complex and the monitored behaviour can be easily confirmed by stockman observations, making use of the system more intuitive, thus increasing the stockman's confidence in the system.

In an embodiment of the present invention, the system comprises a network of sensors attached to the animal. The sensors may be included in a neck collar, head collar, eartag, tail attachment or patches adhered to the skin of the animal or any combination thereof. The sensors are therefore fitted in a non-invasive manner. The sensors may be connected in a bus-like architecture to allow easy addition and removal of sensors as required. Further, the sensors may be reusable.

The sensors may measure location, movement, sound and optical change. The monitor worn by the animal may also include a processor to collect and process information and control communication, software embedded on the processor, a transceiver and a memory store for recording sensor data.

The monitor worn by the animal communicates with an external antenna. The external antenna may comprise a distributed network of antennae provided at different locations. The antennae may download data wirelessly to a local computer system containing a stock management database to be analysed and provide output of prediction and current behaviour/condition of the animals. The analysis is based upon physiological models which can be updated remotely.

The system of the present invention therefore provides effective livestock management and veterinary assistance to predict and react to the onset of conditions such as fertility status, parturition and to detect, at an early stage, lameness of the animals.

The system may be easily extended to predict the onset of disease and predict its epidemiological spread by its links to national or other level databases.

The system may be supplied with various methods of supplying the livestock manager with predictions of conditions; these could include mobile telephone messages, computer screens and milking parlour displays.

The data may be downloaded from the monitor units worn by the animal to the distributed network of external antennae utilising radio protocols such as Bluetooth or Zigbee. The antennae may be placed near congregation points for the livestock, such as feed area, watering troughs, etc. The data may be transferred to a local processor where data analysis is carried out providing information to the stockman and/or uploading a data summary to a regional or national database, where the data is correlated.

The system of the present invention can be utilised to detect the onset of parturition, illness such as lameness and fertility status. The aim is that a network of physical sensors is used to determine behavioural and physiological indicators of condition status and an indication of time of onset of a subsequent condition. Various parameters of the animal are recorded electronically by the monitor unit worn by the animal that can be communicated with any suitably equipped vehicle, market reception, and abbatoir to monitor the health and welfare of an animal as it moves through the food chain. The attachment of the monitor unit is designed to be robust so that it can be worn for long continuous periods as necessary, for example, for the life of the animal. The monitor unit may record a health status record of the animal. This record stored within the monitor unit is then permanently attached to the animal, that is, it is worn for the life of the animal. The data stored may include, for example, birth data, birth location, subsequent lactations, date of parturition, past or predicted health incidents etc.

The monitor unit is a "smart" unit incorporating multiple sensors, a versatile communications infrastructure and multiple behavioural models. The unit of the present invention may incorporate multi-modal sensors incorporating behavioural and physiological analysis to monitor specific conditions in livestock allowing multiple conditions to be monitored simultaneously.

Further, this is achieved according to yet another aspect of the present invention by a device for maintaining an electronic record of condition of livestock, the device comprising: storage means for storing a plurality of records of condition of a subject; means for permanently attaching the device to said subject. Further, some or all of the monitor electronic record may be stored using external storage means e.g. a farm or national database and may be permanently associated with the local monitor electronic record.

In this way various conditions of the animal are recorded electronically by the monitor unit worn by the animal that can be communicated with any suitably equipped vehicle, market reception, and abbatoir to monitor the health and welfare of an animal as it moves through the food chain. The monitor unit is worn permanently by the animal in that it is attached for the life of the animal. The monitor unit may record a health status record of the animal. This record stored within the monitor unit is then permanently attached to the animal. The data stored may include, for example, birth data, birth location, subsequent lactations, date of parturition, past or predicted health incidents etc.

The monitor unit may also receive data from the central computer such as status condition data derived from the sensed data, any environmental data, manually entered status condition data such as actual parturition dates and other observed health issues noted by the stockman, programming data to reprogram the monitor unit.

BRIEF DESCRIPTION OF THE DRAWINGS

For a complete understanding of the present invention, reference is made to the following detailed description taken in conjunction with the accompanying drawings, wherein.

DETAILED DESCRIPTION OF PREFERRED EMBODIMENTS

Figure 1:
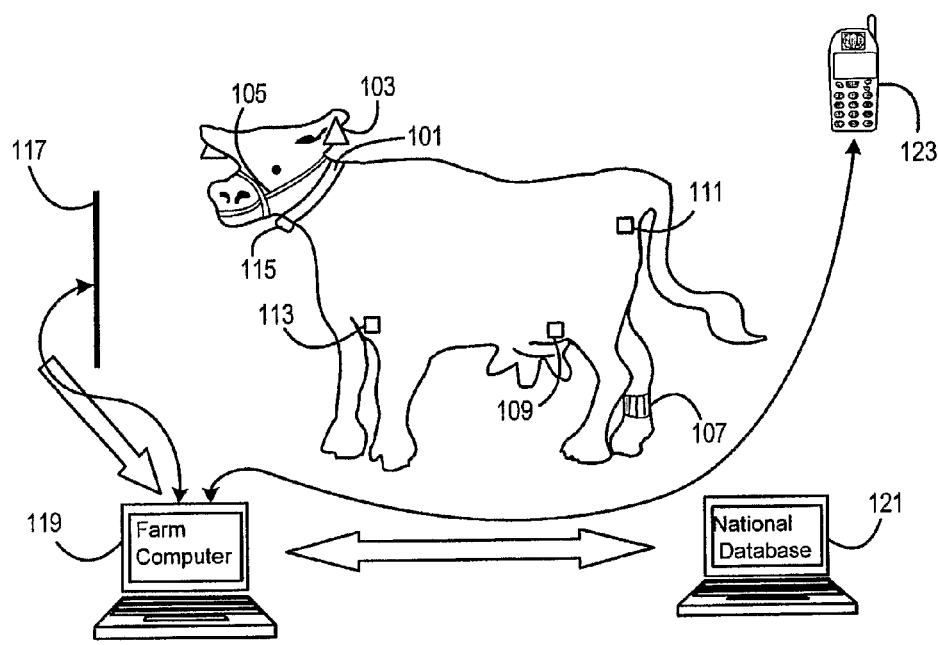
FIG. 1 is a schematic diagram of the system according to an embodiment of the present invention.
Figure 2:
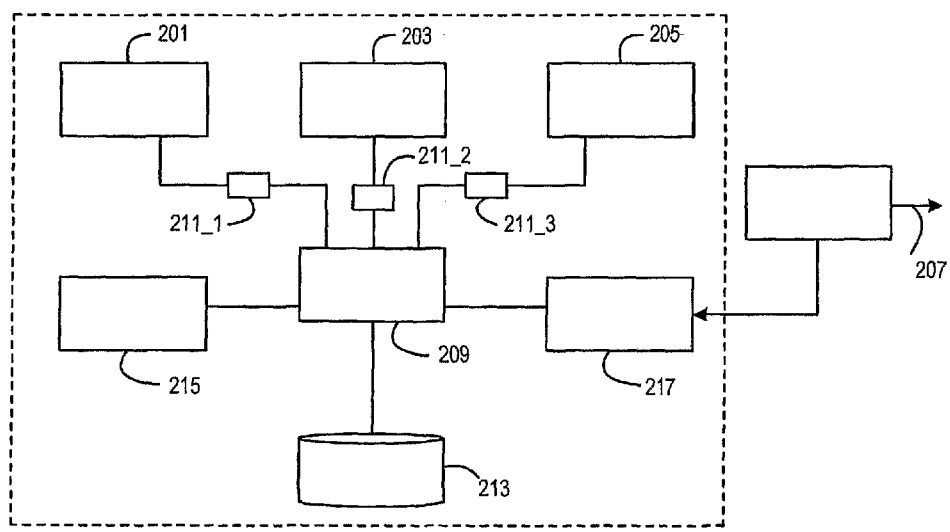
FIG. 2 is a schematic block diagram of the device worn by the animal according to an embodiment of the present invention.

With reference to FIGS. 1 and 2, the system according to an embodiment of the present invention comprises a collar 101 fitted around the neck of an animal. A monitor unit 115 is attached to the neck collar 101. Although, in this embodiment the unit 115 is fitted to a neck collar, it can be appreciated that the unit can be fitted to any convenient fixture device such as for example an ear tag 103, head collar 105, leg attachment 107 or belt (not shown here), transdermal patches 109, 111, ingested bolus 113 or any one of these in addition or in place of the collar 101. The unit 115 is intended to be attached to the animal for continuous monitoring. The attachment needs to be robust to remain attached to the animal for a continuous period, which may in some circumstances be the life of the animal. Although the collar is shown fitted around the neck of a cow, it can be appreciated that the apparatus can be attached to any animal such as for example dairy cow, beef cow, buffalo, sheep, goat, pig, horse and the like.

The collar 101 is fitted to make a snug fit so that it is not slideably moveable along the neck of the animal as the animal head moves up and down extensively such as when the animal is feeding or drinking. The fitting of the collar 101 must be secure to prevent accidental loss during normal activities of the animal such as rubbing against a post and knocking against the bars of a grill on a feeding trough etc. The fixture of the collar 101 may be by means of a buckle, sliding clip etc. The fixture may include a self-tensioning device to maintain a predetermined tension to ensure accurate fitting of the collar.

The unit 115 may be mounted onto the collar 101 or may be formed integral with the collar 101. The collar 101 further comprises an antenna (not shown here) which may be contained in the unit 115 or within the collar 101. The unit 115 comprises a plurality of sensors 201, 203, 205 for monitoring behavioural parameters at least and also sensors for monitoring physiological parameters as shown, for example, in FIG. 2.

FIG. 2 illustrates 3 sensors, a 3-D accelerometer 201, a locator (such as GPS) 203 and a microphone 205. However, any number of sensors may be envisaged such as electromagnetic or field effect sensors, e.g. Hall effect sensors or distance from ground sensors The apparatus may further comprise means for monitoring the distance of the collar above ground. This may be in combination with a sensor to indicate the normal position of the animal's neck with respect to its body. The distance to ground of the collar can provide an indication of whether the animal is standing or lying. This may comprise a range sensor attached to the collar on the underside of the animal's neck, pointing at an angle that, for the median range of what is considered normal neck repose, assumes a vertical or near vertical orientation and therefore provides a vertical range from the sensor location to ground level.

Sensing of the neck orientation may be achieved using inclinometers, tilt or magnetometer sensors providing geometric information, any fixed distance measuring device mounted on the collar on the underside of the animal's neck, can be easily verified against a range of acceptable orientations to supply a valid distance of the neck above ground. Inexpensive distance measuring sensors can be used, such as for example an ultrasonic distance measuring sensor which can provide tolerable accuracies when measuring from fixed reference points projecting to varying ground textures such as grass, straw bedding, concrete flooring etc.

The ability to discriminate standing and lying conditions of an animal can be invaluable in determining a status condition of the animal. For example, during parturition, it is important to know that the animal stands quickly postpartum. This indicates that the mother is able to foster and cleanse its offspring.

The apparatus may further include a plurality of remote sensors 207 positioned elsewhere on the animal outside of the housing of the unit 115 such as sensors for measuring body temperature, humidity, pH of biological fluids, electrical potentials from physiological processes, Hall effects, optical sensors of blood flow or blood oxygenation, vocalisation and respiration, breath and saliva contents, environment temperature and humidity. These remote sensors may be found in an ingested bolus 113, or patches 109, 111. Additional remote sensors may be included in the eartags 103, head collar 105 and/or leg attachment 107. In an alternative arrangement, the unit 115 may be mounted in the eartag 103, head collar 105 or leg attachment 107 etc.

The unit 115 further comprises a local processor 209 which is connected to the sensors 201, 203, 205 via, respective, analogue to digital converters 211_1, 211_2 and 211_3. The plurality of remote sensors 207 is connected to the processor 209 via a wireless link such as short wave radio. The outputs of the remote sensors 207 are digitised via respective analogue to digital converters (not shown here). The unit 115 may further comprise pre-processing means (not shown here) for processing the outputs of the sensors prior to transmission, for example, filtering.

Each remote sensor 207 has a unique identifier associated with a particular animal to prevent remote sensors attached to a neighbouring beast being received and processed by the local processor.

The unit 115 further comprises a local memory store 213, a power source 215 and a transceiver device 217 connected to the processor 209. The power source 215 may comprise replaceable or rechargeable batteries. The unit 115 includes convenient access to a battery housing for replacement etc. of the batteries of the power source 215.

The sensors 201, 203, 205 and 207 are connected via a bus architecture so that additional sensors can be added or removed as required. Preferably the sensors are reusable so that they can be reprogrammed and fitted to another animal etc.

The system further comprises at least one fixed antenna 117. The antenna 117 is provided in a location on the farm where the animal is expected to be in the vicinity of at least once a day so that data collected by the unit 115 can be downloaded. The antenna 117 may be located at the entrance or exit of a milking parlour or at a drinking or feeding trough for example. The antenna may form part of a distributed network of antennae located at various locations such as drinking troughs, sheds, milking parlour etc. The data downloads may be required at more or less frequent intervals. For example, if the output sensory data indicates that the animal is in distress, the system can request via the antenna 117 more frequent downloads. Further, as the predicted parturition date approaches, downloads could be made more frequently, at say, 3 hour intervals. This is possible as many animals are housed in pens as parturition approaches and could therefore be housed in the vicinity of at least one antenna for convenient, frequent downloads.

The system further comprises a local computer (PC) 119 having a display and printer connected thereto. The local computer 119 is remotely connected to a national database 121 via, say, the internet. The local computer 119 may also provide output to a hand-held electronic device 123 such as a mobile telephone or palmtop. The local computer 119 provides 2-way communication with the antenna 117 such that a unit 115 can be reprogrammed or reset by the stockman or reprogrammed automatically to request more frequent downloads for example. Further the two-way communication between the computer 119, antenna 117 and unit 115 allows other data to be transferred to the unit 115.

Figure 3:
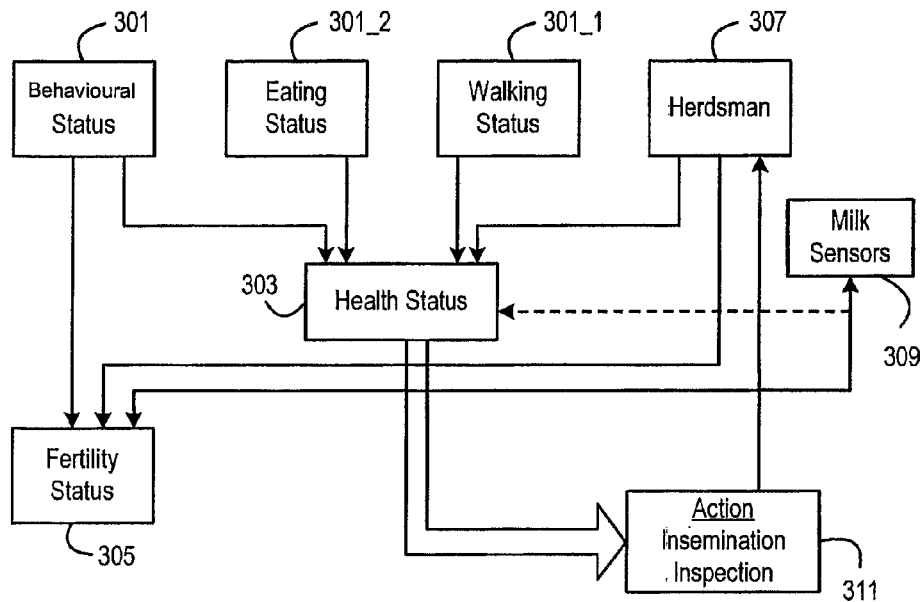
FIG. 3 is a flow chart of the method according to an embodiment of the present invention.
Figure 4:
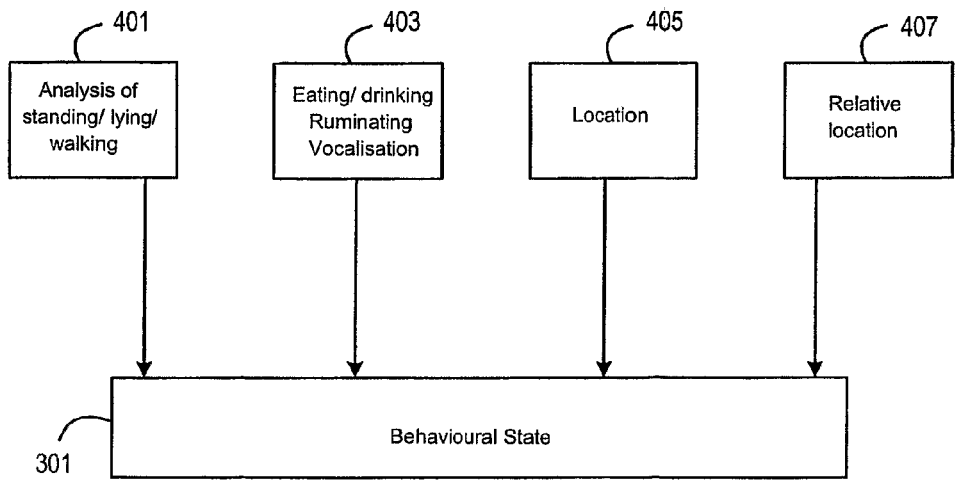
FIG. 4 is a flow chart of the sensory step of the method according to an embodiment of the present invention.

With reference to FIGS. 3 and 4, operation of the apparatus will be described in more detail.

The sensors 201, 203 205, 207 continuously monitor a variety of behavioural (and physiological) parameters of the animal. The digitised output of the sensors 201, 203, 205 and 207 are collated by the processor 209 and are stored in the local memory 213. At predetermined time interval or upon detected of the unit 115 in the vicinity of an antenna 105, the collated data for that time interval is transmitted by the transceiver 217 to the antenna 117. This data is then transferred to the local, farm computer 119. The farm computer 119 stores records for each animal by virtue of the animal's unique identifier which may be stored in its eartag 103. This identifier may be virtually linked to the animal's unique electronic legislative identity. As data is downloaded from the antenna 117 on, say, a daily basis. The farm records can be updated automatically providing the stockman with an updated status of each animal. The updated status of the animal may also be communicated for storage in the local store 213 of the unit 115 such that this data can be downloaded from the unit 115 in the event that the animal leaves the farm. The data stored in the farm computer 119 and/or local store 213 of the unit 115 may include the animal's unique identifier, current condition, for example maiden, pregnant, lactation, number of lactations, days in milk, lame, predicted parturition date, predicted next oestrus (fertility status), suspected illness, of last update where the data is analysed.

The various sensor outputs indicating the behavioural status 301 of the animal is received by the computer system 119 via the antenna 117. This data is compared to a reference physiological data model of the sensory outputs and the behavioural status 301. The 3-D accelerometer 201 records the spatial orientation and movement of the animal's head. This data is analysed by the farm computer 119 to indicate behavioural patterns such as time spent lying, standing, walking 401 and time spent feeding or drinking 403. The microphone 205 records noises made by the animal which can be analysed to indicate time spent eating, ruminating (in the case of a ruminant) and vocalisation 403 and in addition respiration rate and heart rate. The locator 205 provides the location of the animal 405. The relative location 407 may also be monitored. The location data can be analysed to indicate whether the animal is with the herd or keeping up with the herd which may indicate health problems. These are examples only and a number of additional sensory inputs may be analysed to provide additional inputs to the behavioural status 301 of the animal. For example, the additional remote sensors 207 may include monitoring the change of state of a muscle or muscle group or the degree of contraction of a muscle, e.g. Electrohysterogram (EHG), foetal heart rate, body temperature and blood oxygenation.

In a particular example, the output of the accelerometer 201 indicates movement of the animal's head and in combination with the output of the locator 203 indicate when the animal's head is down feeding or drinking. Erratic eating or drinking patterns could indicate that the animal is ill and/or distressed. If the head movement is vigorous during feeding, this would indicate that the animal is healthy. Thresholds of the frequencies of head movement can be set whilst taking into consideration the food type and texture and the age of the animal such that frequency of head movement above the threshold indicates the animal is healthy and below the threshold indicates the animal is ill.

The output date of the sensors 201, 203, 205 can also be used to predict fertility status such as oestrus. It is observed that many animals change their behavioural pattern at this time. They generally become more active, fidget and more agitated. The accelerometer and locator indicate increased walking activity in the animal. Its relative location to the other animals may also provide an indication of fertility status.

The behavioural status 301 of the animal can also be utilised to indicate the general health 303, such for example prediction of the onset of parturition and subsequent lactation, the foetal heart rate indicating health of the unborn, the detection of deviations from a pattern indicating wellness, detection of hypocalcaemia, detection of dystocia, parturition, metritis, lameness, acidosis and ketosis and fertility status 305 such as oestrus. Additional input via the farm computer 119 may be provided by manual input 307 by the stockman and/or milk sensors 309 monitoring milk production etc. Other inputs may be considered such as environment sensed data such as temperature and humidity, weather conditions provided from other sources. The output of the health status 303, fertility status 305 is provided to the stockman via a display or printer for action 311 such as insemination, inspection etc. In this way the system provides an effective way of informing the stockman of various condition status of each animal so that the stockman has better knowledge of the condition of his livestock to enable him to manage feeding, location, bedding, mineral offerings, drug requirements. The predictions provided by the system also enable the stockman to manage more easily farm resources etc. The system may provide an alarm system to indicate an urgent condition status such as difficulties in parturition or indication of serious illnesses such as hypocalcaemia and hypomagnesaemia which require immediate attention.

As illustrated in FIG. 5, an example of a condition monitored by the embodiment of the present invention is illustrated, lameness. Lameness, in particular in dairy cattle, is problematic and therefore it is highly desirable to monitor such a condition in dairy cattle.

Figure 5A:
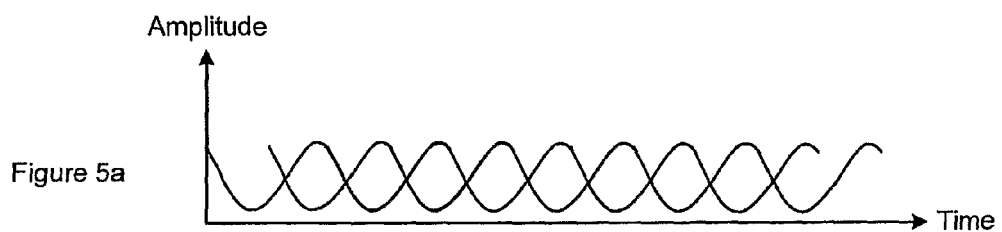
FIGS. 5a, 5b and 5c are a graphical representation of an example of a condition monitored according to the embodiment of the present invention.
Figure 5B:
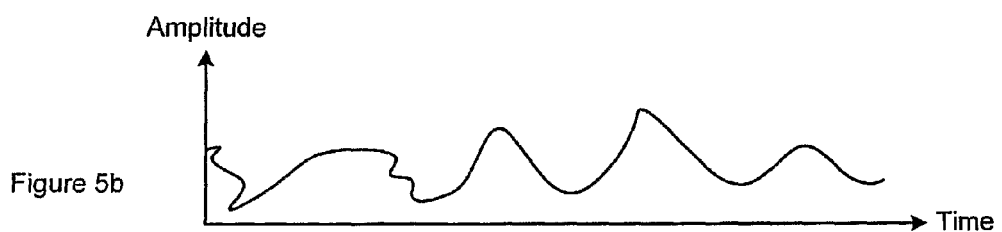
Figure 5C:
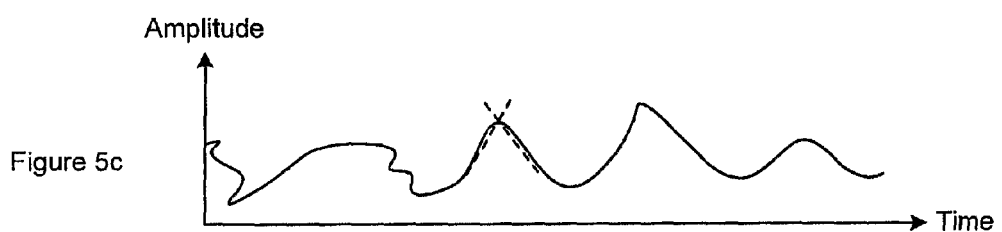

As illustrated in FIG. 5a, the normal gait of an animal is represented generally as a smooth, rhythmic head movement which is detected by the accelerometer sensor 201. However, in a lame animal the movement is more erratic with jerky movements as illustrated in FIG. 5b. This output is analysed by the farm computer, for example by counting novel singularities or measuring the change of slope or integrating area under an RMS or by FFT of the frequency data to detect anomalies as illustrated in FIG. 5c. Numerous mathematical techniques are available and can be overlaid to extract features from the data.

Although a preferred embodiment of the method and system has been illustrated in the accompanying drawings and described in the foregoing detailed description, it will be understood that the invention is not limited to the embodiment disclosed, but is capable of numerous variations, modifications without departing from the scope of the invention as set out in the following claims.

The invention claimed is:

1. A method for monitoring the condition of livestock, the method comprising the steps of:

sensing, with a plurality of sensors, a plurality of orientation and movement parameters of an animal's head;

using a processor configured with computer executable instructions to derive a plurality of different behavioural parameters of said animal from said sensed plurality of orientation and movement parameters, said plurality of different behavioural parameters including at least one of walking activities of said animal, standing activities of said animal and lying activities of said animal, using said processor to determine a plurality of status conditions of said animal from said derived behavioural parameters, said status conditions including at least one of fertility, oestrus and prediction of onset of parturition; and transmitting, with a transmitter, said plurality of orientation and movement parameters, said plurality of different behavioural parameters, or said determined plurality of status conditions, wirelessly, to a central computer.

2. The method according to claim 1, wherein said plurality of different behavioural parameters further includes at least one of:
absolute location of said animal;
relative location of said animal to another animal;
feeding activities of said animal; and
drinking activities of said animal.

3. The method according to claim 1, wherein the method further comprises the step of:
sensing at least one physiological parameter of said animal; and wherein said sensed physiological parameter is transmitted, wirelessly, to said central computer; and wherein said plurality of status conditions are determined on the basis of said transmitted, sensed, behavioural conditions or said transmitted, sensed, physiological parameter.

4. The method according to claim 3, wherein said at least one physiological parameter includes one of:
breathing rate;
heart rate;
heart rate variability;
body temperature;
breath contents;
saliva contents;
change of state of at least one muscle or muscle group; and
degree of contraction of at least one muscle or muscle group.

5. The method according to claim 1, wherein the conditions include:
lameness;
infection; and
nutritional disorders.

6. The method according to claim 1, wherein the method further comprises:
storing said determined status conditions of said animal in a unit, permanently attached to said animal.

7. A system for monitoring the condition of livestock, the system comprising:
a plurality of sensors configured to sense a plurality of orientation and movement parameters of an animal's head;
a processor configured with computer executable instructions to derive a plurality of different behavioural parameters of said animal from said sensed plurality of orientation and movement parameters, said plurality of different behavioural including at least one of walking activities of said animal, standing activities of said animal, and lying activities of said animal, and determine a plurality of status conditions of said animal, said status conditions including at least one of fertility, oestrus and prediction of onset of parturition; and at least one transmitter configured to transmit said plurality of orientation and movement parameters, said plurality of different behavioural parameters, or said determined plurality of status conditions, wirelessly, to a central computer.

8. The system according to claim 7, wherein said plurality of sensors are attached to said animal.

9. The system according to claim 8, wherein said plurality of sensors are attached non-invasively.

10. The system according to claim 7, wherein said plurality of sensors are connected in a network.

11. The system according to claim 7, wherein the system further comprises at least one fixed antenna configured to receive said transmitted orientation and movement parameters, behavioural parameters, or status conditions.

12. The system according to claim 11, wherein the transmitted orientation and movement parameters, behavioural parameters, or status conditions received by the antenna is downloaded to said central computer.

13. The system according to claim 7, wherein the system further comprises at least one receiver for receiving data from said central computer.

14. A device for monitoring the condition of livestock, the device comprising:
attachment means for attaching the device to an animal;
a plurality of sensors configured to sense a plurality of orientation and movement parameters of an animal's head;
a processor configured with computer executable instructions to derive a plurality of different behavioural parameters of said animal from said sensed plurality of orientation and movement parameters, said plurality of different behavioural parameters including at least one of walking activities of said animal, standing activities of said animal and lying activities of said animal, and determine a plurality of status conditions of said animal, said status conditions including at least one of fertility, oestrus and prediction of onset of parturition; and
a transceiver configured to transmit said plurality of orientation and movement parameters, said plurality of different behavioural parameters, or said determined plurality of status conditions, wirelessly, to a central computer.

15. The device according to claim 14, wherein said plurality of sensors are attached non-invasively.

16. The device according to claim 14, wherein at least one of said plurality of sensors is reusable.

17. The device according to claim 14, wherein said plurality of sensors are connected in a network.

18. The device according to claim 14, wherein the device is remotely programmable.

19. The device according to claim 14, wherein said attachment means comprises a collar, ear tag, halter, belt, tail tag or adhesive patch.

20. The device according to claim 14, wherein said transceiver receives data from said central computer.

21. The device according to claim 20, wherein said received data includes sensed data, condition data, environmental data, manually entered status condition data, or programming data.

22. The device according to claim 14, wherein said device further comprises:
storage means configured to store status condition data of said animal.

* * * * *